United States Patent [19]
Armstrong

[11] Patent Number: 5,830,507
[45] Date of Patent: Nov. 3, 1998

[54] BIOTHERAPEUTIC CELL-COATED MICROSPHERES

[75] Inventor: David W. Armstrong, Ottawa, Canada

[73] Assignee: National Research Council of Canada, Ontario, Canada

[21] Appl. No.: 338,596

[22] PCT Filed: Apr. 23, 1993

[86] PCT No.: PCT/CA93/00187

§ 371 Date: Nov. 18, 1994

§ 102(e) Date: Nov. 18, 1994

[87] PCT Pub. No.: WO93/23088

PCT Pub. Date: Nov. 25, 1993

[30] Foreign Application Priority Data

May 18, 1992 [GB] United Kingdom .................... 9210574
Apr. 23, 1993 [WO] WIPO ...................... PCT/CA93/00187

[51] Int. Cl.$^6$ .............................. A61K 9/16; C12N 11/00; C12N 11/02; C12N 11/08

[52] U.S. Cl. ........................... 424/489; 424/490; 435/174; 435/177; 435/180; 435/240.1; 435/240.2; 435/240.23; 435/240.24; 623/15

[58] Field of Search ..................................... 424/450, 489, 424/490–500; 435/174–182, 240.1–240.243; 623/15

[56] References Cited

U.S. PATENT DOCUMENTS

| 4,906,577 | 3/1990 | Armstrong et al. ..................... 435/313 |
| 4,996,154 | 2/1991 | Gabriels, Jr. .............................. 435/240 |
| 5,135,915 | 8/1992 | Czarniecki ................................. 514/21 |
| 5,618,531 | 4/1997 | Cherksey ............................... 424/93.7 |

FOREIGN PATENT DOCUMENTS 9012604  11/1990  WIPO .

OTHER PUBLICATIONS

Beumar et al. "Biocompatibility and Characterization of a Polymeric Cell–Seeded Skin Substitute" *17th Ann. Meeting Soc. For Biomaterials*, May 1–5 1991, Scottsdale, AZ, p. 263.

Demetriou et al. "Replacement of Liver Function in Rats by Transplantation of Microcarrier–Attached Hepatocytes" *Science* 233: 1190–1192 (Sep. 12, 1986).

Bagot et al. "Reconstructed human epidermis: absence of Langerhans cells and failure to stimulate allogeneic . . . " *Clin. Exp. Immunol.* 71: 138 (1988).

van Wezel. "Growth of cell–strains and primary cells in microcarriers in homogenous culture" *Nature* 216: 64–65 (Oct. 7, 1967).

Bibel et al. "Antimicrobial Activity of Sphingosines" *J. Invest Dermatol.* 98: 269–273 (1992).

McMillan et al., *J. Burn Care Rehab.* 6: 444–446 (1985).

*Primary Examiner*—Gollamudi S. Kishore
*Attorney, Agent, or Firm*—Sughrue, Mion, Zinn, Macpeak & Seas, PLLC

[57] ABSTRACT

A living skin replacement for the treatment of partial-thickness and full-thickness skin injuries, such as burns and other wounds, consists of a slurry of cell-coated microspheres which can be applied to the skin injury in much the same manner as a paste or salve. The skin implant can accommodate contour variations across the often extensive area of a skin injury and does not require the use of stapling, suturing or other attachment methods. The microspheres can be formed of a variety of materials that are biocompatible and resorbable in vivo.

38 Claims, 6 Drawing Sheets

BIOTHERAPEUTIC CELL-COATED MICROSPHERES

This application is a 3717 PCT/CA93/00187 filed Apr. 23, 1993

TECHNICAL FIELD

The present invention relates to the field of tissue implants and more particularly to the application of skin implants for the treatment of full- and partial-thickness skin injuries, such as burns and other wounds.

BACKGROUND ART

Full-thickness and partial-thickness skin injuries, such as burns and other wounds, represent a significant cost to health care systems. For example, about 2 million people in North America suffer from burns each year. Of these about 200,000 people are hospitalized, 15,000 of which die of burn-related causes. The overall hospital cost for treating these patients is in the order of $1000/percentage burned area ($U.S., 1992) so that the average burn patient with burns to 20 to 30% of their body generates initial hospital care costs of about $25,000, not including the cost of further treatment and potential loss of productivity and income. For instance, McMillan et al (J Burn Care Rehab 6:444–446; 1985) have demonstrated that operating room expenses increase logarithmically with the percent of body surface area burned. Clearly, there is a requirement for advances in technology to mitigate these costs and to reduce the suffering of the patients.

Skin consists of a dermal layer which underlies an epidermal layer. The dermal layer consists mostly of fibroblasts and is about five times the thickness of the epidermal layer. The epidermal layer of intact skin, consisting mainly of keratinocytes and immune cells such as dendritic Langerhans cells, normally prevents water loss and microbial invasion, so that full- and partial-thickness skin injuries can be life-threatening. The rate of wound closure to prevent the escape of essential body fluids and the invasion of bacteria is therefore a vital factor in the recovery of the patient. Accordingly a wide array of wound coverings has been developed to expedite wound closure.

An existing treatment of burns and wounds includes the use of the patient's own skin, or cadaver- or porcine-derived tissue for grafting onto the wound of the patient. Traditional patient-derived skin graft (autograft) techniques are generally very painful to the patient who is already suffering from the burn or other wound. An autograft is comprised of a substantial thickness of both the epidermal and dermal layers of the skin taken from another site on the body. In an attempt to limit the amount of skin taken and therefore the size of the new wound, the autograft is treated to form a lattice pattern across the skin injury. However, the lattice pattern in the dermis layer of the autograft are subsequently filled with permanent scar tissue in vivo. These scars are often very large and can be severely disfiguring or, depending on their location, can cause dysfunction. Furthermore, the patient may not have enough non-burned area in order to salvage a large enough graft for transplant to another location of the body.

Skin grafts derived from cadavers (allograft) or porcine (xenograft) sources have been used in an effort to reduce the suffering of the patient and to encourage wound healing. A major drawback of the allograft is the possibility of disease transmission (for example, HIV, hepatitis B). Moreover, the epidermal layer shows marked antigenicity so that grafts, including allografts, not derived directly from the patient are usually rejected within two weeks of implant. While the xenograft provides a graft when there is a shortage of human donor tissue, it is rejected even more rapidly than the allograft and must be removed on the third day after application before drying and sloughing and before strong adhesion to the wound necessitates surgical excision.

All of these skin grafts, namely the autograft, allograft, and xenograft, are normally very thin and fragile, making transport and handling thereof extremely difficult. Furthermore, the grafts are attached to the wound site with often extensive suturing and/or stapling adding significantly to the discomfort of the patient. Additionally, severely burned or wounded patients are already compromised thereby making surgical procedures under anaesthesia even more difficult and possibly life-threatening.

In more recent developments, for example U.S. Pat. No. 4,996,154 (issued Feb. 26, 1991 to Millipore Corp, U.S.A.) and Beumar, G.J. et al ("Biocompatibility and Characterization of a Polymeric Cell-Seeded Skin Substitute", 17th Ann Meeting Soc for Biomaterials; May 1–5, 1991, Scottsdale, Ariz., U.S.A., p. 263), skin cells have been grown on mesh-type sheets to constitute a tissue implant. The sheets are sutured or stapled in place on the wound area and the support material is eventually resorbed by the body. There is some indication from preliminary studies that the degree of scar tissue development can be reduced by this approach. As well, the mesh matrix patch is more stable than a skin graft.

However, there are a number of problems with the planar cellular films or sheets of regenerated skin. The mesh matrix skin patches are typically supplied in dimensions of about 10 cm wide by 10 cm long and of only a few cell layers thick. It will be appreciated by those skilled in the art that burn sites are often larger and rarely of uniform thickness or of planar structure. The patches do not adequately account for contour variations in the skin so that the problem of disfigurement still exists to a greater or lesser degree in most cases. While they are more stable than grafts, the thin patches are still very fragile and in many instances the thin sheets are strengthened with petroleum jelly impregnated gauze for surgical procedures. Additionally, the small pieces of skin must still be sutured and/or stapled to each other and onto the body resulting in a prolongation of the surgical procedure on an already weak and compromised patient.

Furthermore the applied skin patches can have very poor gas/mass transfer characteristics leading to the potential for tissue necrosis due to lack of nutrients reaching the cells. This, in turn, can lead to blistering of the patch. Gas and mass transfer can be further adversely affected by a residual layer of petroleum jelly on the site once the gauze is removed following the surgical procedure. The residual layer of petroleum jelly can even lead to partitioning of various factors, such as growth factors, into this layer where they would not be available for subsequent action on the cells.

Another drawback lies in the actual cultivation of the skin-derived cells in vitro. Typically these anchorage-dependent cells are grown under static conditions in a tissue culture flask containing the mesh matrix in relatively small volumes of a culture medium so that passive gas transfer from the surface of the medium to the cells at the bottom of the flask can be effected. Depletion of nutrients from the medium is a major concern which may be compounded by the formation of a microenvironment immediately adjacent the cells. Such a microenvironment is even further depleted of nutrients and tends to have a higher concentration of metabolic by-products which adversely affect the growth of the cells. In order to overcome these problems, numerous labour-intensive steps are required to change the medium, each step adding another possibility for microbial contamination.

In an effort to increase gas/mass transfer, a culture system comprised of a gas permeable bag with a recirculating pump has been developed (Marrow-Tech Inc., U.S.A.) to move media across the surface of the growing culture on a mesh fabric contained within. The cells are typically seeded randomly on the mesh thereby creating "multi-nuclei" of cell growth. However, any cells that are not firmly anchored to the surface will likely circulate through the pump and experience shear and other disruptive effects. The system is still labour intensive and cumbersome leading to an increased chance of contamination due to excessive handling requirements. While the system is not static, the environment is not totally homogeneous and the cells anchored to the mesh are not of a uniform growth phase due to the semi-static culture conditions and the random seeding of cells on the mesh. Not only is there a problem of homogeneity across a single patch, there is also a problem of homogeneity from patch to patch across the often extensive area of the skin injury. Moreover, the effective area of viable cells can be significantly reduced by suturing and/or stapling at the edges of the patch which can destroy or disrupt the proliferation of cells.

None of the prior art techniques accounts for contour variations of the skin injury. Rarely would a skin injury be "perfectly" shaped to accept these planar grafts and patches, resulting in the probable occurrence of non-contact areas where new skin does not fully establish. All of these implants require stapling and/or suturing thereby increasing the likelihood of further scarring.

Moreover, many of these developments fail to address the critical need to establish an epidermal layer. Water vapour passes through normal skin at a rate of about 8.5 g/m$^2$ per hour and from sites without an epidermal layer at a rate of about 150 g/m$^2$ per hour. Ideally, the permeability of a skin implant should approach that of normal skin to prevent tissue drying and thrombosis when permeability is too high and liquid accumulation and low adherence of the graft at low permeability.

Demetriou, A. A. ("Replacement of liver function in rats by transplantation of microcarrier-attached hepatocytes" *Science* 233:1190–1192; Sep. 12, 1986) describes attachment of hepatocytes to collagen-coated cross-linked dextran microcarriers for subsequent implantation in the peritoneal cavity of rats. The microcarriers are used to provide a surface for attachment so that the hepatocytes survive and function in vivo. The microcarriers are not intended to resorb or degrade once implanted.

International Application Number PCT/US90/02257 (Vacanti et al, published Nov. 1, 1990, WO 90/12604) relates to an implant of large volumes of cells on polymeric matrices. The matrix is a fibrous biocompatible degradable or non-degradable sheet material having an interstitial spacing of 100–200 μm. Vacanti et al describe the attachment and growth of hepatocytes to the matrix for subsequent implant in the mesentery of the small intestine.

An object of the present invention is to provide a living skin replacement for the treatment of full- and partial-thickness skin injuries, such as burns and other wounds, which can accommodate contour variations. It is a further object of the present invention to provide an implant having a dermal layer and a functional epidermis which does not require the use of stapling, suturing, or other attachment methods.

DISCLOSURE OF INVENTION

According to one aspect of the present invention there is provided a living skin replacement for full-thickness and partial-thickness skin injuries characterized in that it comprises a plurality of microspheres, the microspheres formed of a material which is biocompatible and resorbable in vivo, and a culture of skin cells coating the microspheres, whereby the microspheres coated with skin cells are applied to the skin injury.

According to another aspect of the present invention there is provided a process for the production according to a living skin replacement characterized by the steps of culturing skin cells, providing a plurality of biocompatible, resorbable microspheres, attaching the skin cells to the microspheres, and growing the attached skin cells to confluence or near confluence in a growth medium, and thereafter concentrating the cell-coated microspheres into a slurry by removing some or all of the medium.

According to yet another aspect of the present invention there is provided a method of use of cell-coated microspheres for treating a full-thickness or partial-thickness skin injury, characterized by the steps of growing cells derived from a dermal layer of skin on biocompatible, resorbable microspheres in a medium, concentrating the microspheres coated with cells into a slurry by removing some or substantially all of the medium, and applying the slurry of cell-coated microspheres onto an area of skin injury.

BRIEF DESCRIPTION OF DRAWINGS

In drawings which illustrate embodiments of the present invention.

BEST MODE FOR CARRYING OUT THE INVENTION

In accordance with the present invention, cells are attached to microspheres for subsequent implant in vivo. In particular, a slurry of skin cell-coated microspheres is used as a living skin replacement for full- and partial-thickness skin injuries. The slurry of cell-coated microspheres is applied directly to the skin injury in much the same way as a salve or paste.

The skin cells can be derived from a relatively small tissue explant from a patient. Alternatively, dermal fibroblasts, which exhibit low allergenicity in transplants, can be derived from a donor, including a cadaver. The epidermal layer shows marked antigenicity so that implants of this layer normally need to be derived directly from the patient. Studies suggest, however, that the Langerhans cells are largely responsible for the antigenicity of the epidermal layer (Bagot, M. et al, Clin Exp Immunol 71:138; 1988). It is therefore possible that a pure culture of keratinocytes could be derived from a donor and that rejection thereof would be minimal or absent.

In accordance with the present invention, a small tissue explant, typically 4 cm$^2$, is obtained from the patient or donor using a dermatome or other suitable surgical instrument. The explant could include the epidermal layer alone or a combination of the epidermal and dermal layers. The tissue is then dissociated using conventional enzyme and processing techniques and seeded either into tissue culture flasks for subsequent cell expansion of the fibroblasts and/or the keratinocytes. The cells of the dermal and epidermal layers can be separated with enzymes such as dispase or by soaking in culture medium or phosphate buffered saline or by other well established techniques. It will be appreciated by those skilled in the art that a "bank" of donor-derived, including cadaver-derived, skin cells could be established for prompt treatment of skin injuries.

The microspheres have a diameter in the range of about 50 to 500 μm, and preferably in the range of about 80 to 250 μm. The microspheres can be made of a variety of materials as will be discussed in more detail hereinafter. The important consideration in the choice of microsphere is that the material thereof must be biocompatible and should be capable of being resorbed into the body without the formation of toxic byproducts. One suitable material is polyhydroxybutyrate (PHB) which is conventionally used for resorbable surgical staples and suture materials. PHB is resorbed in vivo with the ultimate end products being carbon dioxide and water. Other suitable materials are lactide-glycolide polymers which are commercially available for use in drug delivery systems (Medisorb Technologies International, USA). The polymers are absorbed by random hydrolysis of the ester linkages and are broken down into lactic and glycolic acids, which are normal metabolic by-products.

In one embodiment of the present invention, dermal fibroblasts isolated from a patient- or donor-derived tissue explant are cultured in a tissue culture flask until a sufficient number of the cells is produced. Typically, it is desired to have a sufficient number of cells to provide a viable cell density in the bioreactor of about or at least $10^4$ to $10^5$ cells/ml. In a typical microsphere loading of 3 to 5 mg/L with approximately $5 \times 10^6$ microspheres/g dry weight this cell density corresponds to approximately 5 cells/microsphere.

When a sufficient number of cells has been produced, the cells are detached from the bottom of a tissue culture flask using, for example, trypsin. It will be appreciated by those skilled in the art that a number of passages may be required in different sized tissue culture flasks to achieve the desired number of cells. The cells are then seeded in a bioreactor containing a suitable cell culture medium and microspheres at a density of 1 to 25 g/L with an optimal level of between 2 and 5 g/L. The microspheres can be added to the culture medium immediately prior to cell-seeding or the microspheres may be pretreated by soaking in the medium for a length of time prior to cell-seeding. The cells are then allowed to attach to the microspheres under static or semi-static conditions for a prescribed length of time, for example 3 to 6 hours.

Figure 1:
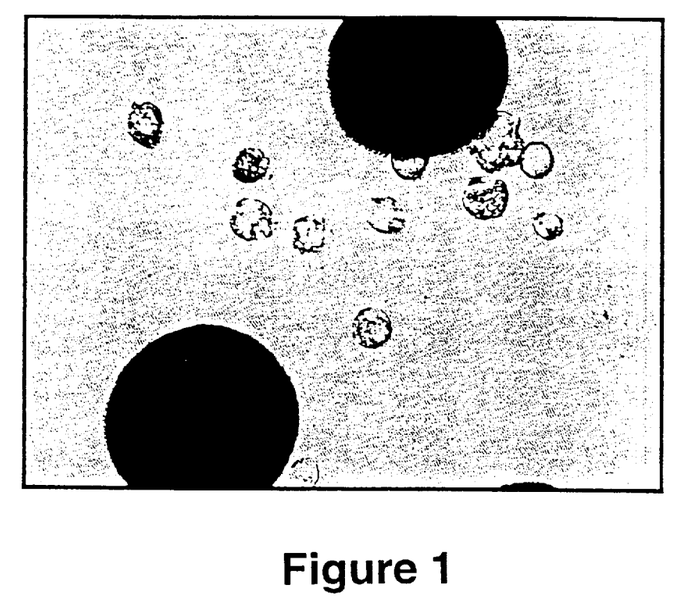
FIG. 1 is a micrograph showing dermal fibroblasts attached to microspheres at 1 hour post cell-seeding.

The attachment step can be performed in a reduced volume of medium with intermittent agitation for a few minutes every half hour for approximately 3 to 6 hours. FIG. 1 is a micrograph showing neo-natal foreskin derived dermal fibroblasts attached to PHB-PHV (polyhydroxybutyrate-polyhydroxyvalerate copolymer) microspheres at 1 hour post cell-seeding. The dermal fibroblasts are starting to attach to the microspheres.

Figure 2:
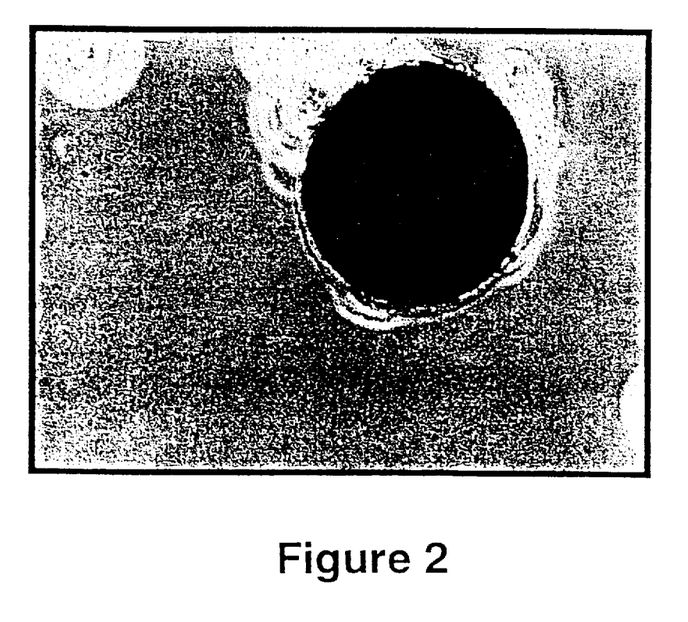
FIG. 2 is a micrograph showing the dermal fibroblasts attached to microspheres of FIG. 1 at 22 hours post cell-seeding.

After a period of time to allow further cells to attach to the microspheres, the remainder of the medium is then added to provide the desired working volume with continuous agitation of the cell-coated microspheres thereafter. FIG. 2 is a photomicrograph showing the dermal fibroblasts attached to PHB-PHV microspheres of FIG. 1 at 22 hours post cell-seeding. The majority of the dermal fibroblasts that have attached to the microsphere have become flattened and are no longer spherical.

Alternatively, the dissociated cells from the tissue explant can be seeded directly into a bioreactor. For example, a 4 cm$^2$ tissue explant yields about $2-5 \times 10^7$ cells which is sufficient to provide a seeding density of between 3 and 5 cells/microsphere in 1 L of medium.

The dermal fibroblast cells, attached to the microspheres, are then grown in suspension culture in a bioreactor, which may conveniently have a working volume of 250 ml to several litters. It is possible to provide a substantial skin implant with the cells cultured in a 1 L bioreactor. Based on an average surface area of 5000 cm$^2$/g dry weight microspheres, a microsphere density of between 3 and 5 mg/ml provides an effective surface area of about 2 to 2.5 m$^2$ in a 1 L working volume vessel. The cells eventually cover this surface area creating a comparable layer of skin for further migration and proliferation in vivo.

Smaller area burns can be treated with the culture from a smaller vessel including a 250 ml-spinner flask. A sophisticated bioreactor can be employed, with all environmental parameters carefully controlled and monitored, for example, as described in U.S. Pat. Number 4,906,577 (Armstrong, Fleming, & Grenzowski) issued Mar. 6, 1990. Alternatively, a simple stirred container in a $CO_2$ incubator can be used. From the initial cell-seeding of the microspheres to the final harvesting of cell-coated microspheres from the bioreactor, protocol to maintain sterility within the vessel has been well-established in the art.

Unlike the static or near-static cell culture techniques, as are practised for the mesh matrix patches discussed previously, the growth of cells in suspension in a bioreactor provides greater unit productivity. This has been proven by developments in suspension culture of cells attached to microcarriers, which are small beads having a diameter in the range of 100 to 200 μm with a surface area of about 5000 cm²/g, and are typically made of cross-linked dextran. Certain cell lines have been grown on microcarriers to improve the unit productivity for cell growth and/or product formation over that achievable in static culture in tissue culture flasks (van Wezel, A. L. "Growth of Cell-Strains and Primary Cells in Micro-carriers in Homogeneous Culture" *Nature* 216:64–65; Oct. 7, 1967).

Static cultures for the production of skin grafts on support mesh sheets, in tissue culture containers, have an effective surface/volume ratio (S/V) of about 2–5 cm$^{-1}$ compared to an S/V of about 150 cm$^{-1}$ for microspheres suspended at a concentration of 25 g/L. Furthermore, suspension culture is less labour-intensive and the culture is homogeneous so that problems of gas transfer, depletion of nutrients, and accumulation of nutrients are not as restrictive. For example, for the production of 2 m of new tissue using the mesh matrix, approximately 250 tissue culture flasks would be required, based on a typical available surface area of 80 cm² per flask.

Preferably, the dermal fibroblast cells are grown in the bioreactor until they reach a state of confluence or near confluence, at which point the cells substantially coat the microsphere. Confluence is typically achieved in about 7 days. However it is possible to use the cell-coated microspheres therapeutically before this time at a point of near confluence when the cell population is still in a highly migratory and proliferative state. The cells are then concentrated by removal of excess culture medium and washed in situ with an appropriate buffer or solution to form a microsphere/cell slurry. contrary to the normal practice of microcarrier culture which then uses an agent such as trypsin to remove the cells from the microcarriers, in the present invention, the dermal fibroblast cells are not removed from the microspheres. The microsphere/cell slurry is then applied directly on the wound in much the same way as a salve or paste would be applied. Owing to the uniform suspension of microspheres, each microsphere has a similar number of cells attached thereto resulting in a homogeneous population for subsequent application on the skin injury. Moreover, there is homogeneity of the growth phase of the cells across the area of the skin injury, even in the case of an extensive area.

Unlike the mesh matrix patch discussed previously, the present invention reduces the required number of manipulations of the cells. This, in turn, reduces the potential for damage to the cells themselves and minimizes the chances of contamination leading to wound infection.

Cells applied to a wound in accordance with the present invention can be easily delivered to the entire surface of the wound. This is a very important advantage since cells grown on a mesh matrix, and even patient-derived skin grafts, will often have many non-contact areas where the skin may not fully establish. The consistency of the slurry allows for correction of contour variations that may be present in a wound. This is a great advantage over the planar implants of the prior art because, firstly, a wound is rarely of uniform depth with a smooth flat base and, secondly, the wound may extend across a significant area. For example, it will be appreciated by those skilled in the art that, in the treatment of a burn extending the length of the arm on the underside thereof, there are many natural curves along its length. The present invention provides an implant that can fill even the deepest wound for effective healing thereof and more natural, tridimensional tissue regeneration at the injury site.

Figure 3A:
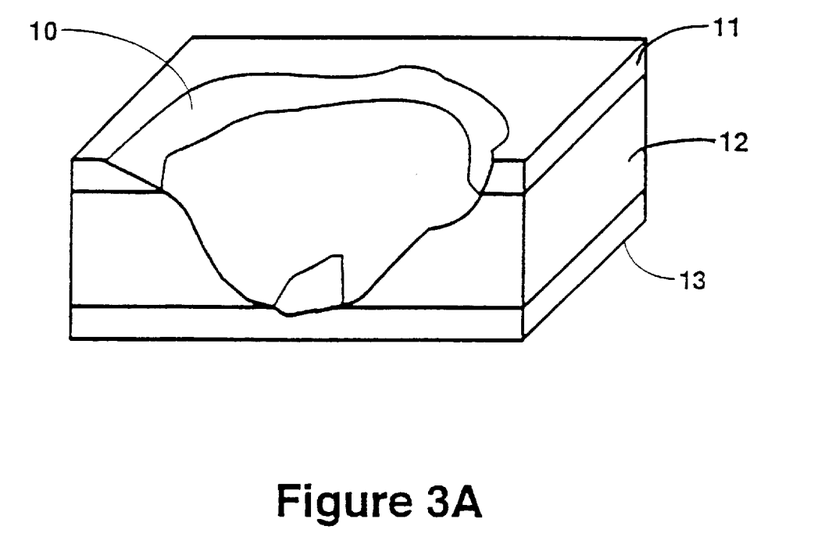
FIG. 3A is a schematic representation of a full-thickness skin injury.

An example of an irregular full-thickness skin injury 10 is shown in FIG. 3A. The skin injury 10 extends through the epidermis 11 and the dermis 12 to the underlying muscle 13.

Figure 3B:
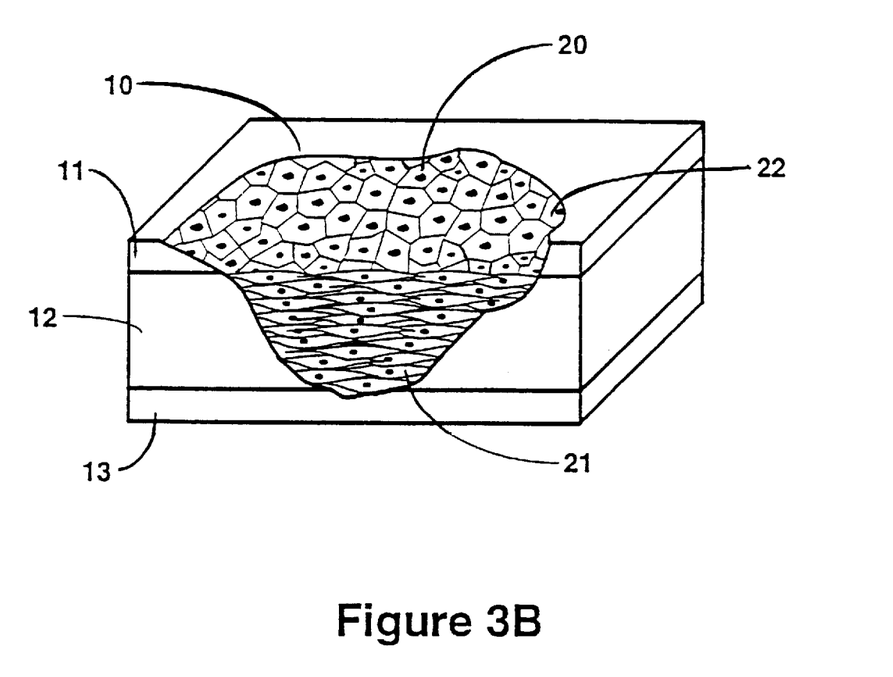
FIG. 3B is a schematic representation of the full-thickness skin injury of FIG. 3A implanted with a living skin replacement of the present invention.

It will be appreciated by those skilled in the art that a planar skin graft would not provide an adequate skin implant for this type of injury. FIG. 3B is a schematic representation of the same skin injury 10 implanted with a living skin replacement 20 of the present invention. The living skin replacement 20 provides an implant of dermal fibroblasts 21 and keratinocytes 22.

Subsequent layers of dermal fibroblasts may be applied to the wound over the first layer of dermal fibroblasts, for example, to correct any further contour variations. It is also possible that a donor-derived dermal fibroblast/microsphere slurry may be applied to the wound followed by an application of a patient-derived dermal fibroblast/microsphere slurry.

The use of cells at or near confluence on the microspheres not only provides a higher concentration of cells to the skin injury but the effectiveness of the cells is also increased. Animal cells tend to function better if they are in a microcosm such as that found in a confluent or near confluent cell population on a microsphere. Better production of growth and spreading factors are also achieved especially with cells in close contact with each other because of intercellular regulation including autocrine and paracrine interactions, less diffusional limitations, etc.

The application of the dermal layer allows for rapid production of the structural protein collagen and other growth and attachment factors. Early application of dermal fibroblasts can minimize or prevent contraction of the skin which is the major cause of scarring and excess fluid loss. Dermal fibroblasts can differentiate and align in an axial fashion in a wound to effectively hold the wound together especially if the skin injury is a longitudinal cut. The early application of microspheres coated with fibroblasts leads to better wound healing and reduces the suffering of the patient.

Once the slurry is applied to the wound a gaspermeable wound dressing may be used to cover the site. The dermal fibroblasts of the microsphere/cell slurry then migrate and grow off the microspheres into the surrounding tissue to produce a continuous surface in place of the skin injury. With the passage of time and as the cells grow, the microspheres start to resorb in vivo.

Preferably the skin implant also includes the regeneration of the epidermal layer. While the dermal fibroblast layer is being established in vivo, cells from the epidermal layer of the patient can then be cultured in a tissue culture flask. When a sufficient number of cells has been produced, the cells are removed from the bottom of the tissue culture flask using, for example, trypsin. The cells are then seeded in a bioreactor containing a suitable cell culture medium and microspheres. As previously discussed, another option is to use epidermal cells from a patient-derived tissue explant to inoculate the microspheres directly. The cells are allowed to attach to the microspheres and cultured in suspension in a bioreactor in the same manner as described earlier for the dermal fibroblasts. It will be appreciated by those skilled in the art that the use of a broad spectrum antibiotic in the initial phase of cell proliferation may be required owing to the likelihood of wound site contamination from the normal skin flora and that imparted from other sources.

Figure 4:
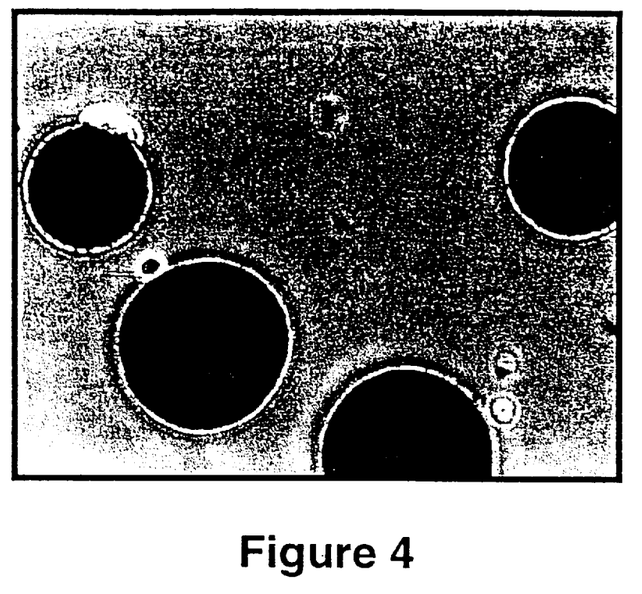
FIG. 4 is a micrograph of keratinocytes attached to microspheres at 24 hours post cell-seeding.

FIG. 4 is a micrograph of neo-natal foreskin derived keratinocytes attached to PHB-PHV microspheres at 24 hours post cell-seeding. The majority of the keratinocytes that have attached to the microspheres are flattened and no longer spherical.

Figure 5:
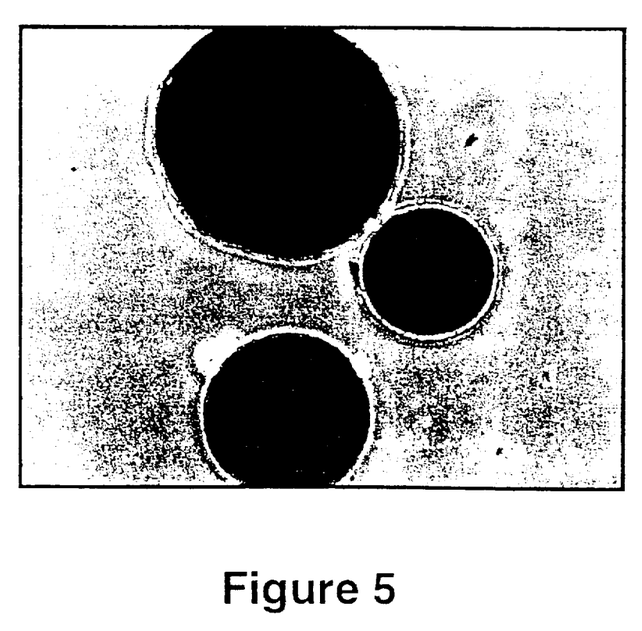
FIG. 5 is a micrograph of keratinocytes attached to microspheres at 24 hours post cell-seeding. The microspheres were incubated in culture medium for 24 hours prior to cell-seeding.

As mentioned previously, the microspheres can be added to the culture medium immediately prior to cell-seeding or the microspheres may be pretreated by soaking in the medium for a length of time prior to cell-seeding. FIG. 5 is a micrograph of neo-natal foreskin derived keratinocytes attached to PHB-PHV microspheres at 24 hours post cell-seeding. The microspheres were incubated in culture medium for 24 hours prior to cell-seeding. The majority of the keratinocytes that have attached to the microspheres are flattened.

When the epidermal cells, including keratinocytes, reach confluence or near confluence on the microspheres, some or all of the culture medium is removed, resulting in a slurry of cell-coated microspheres. The wound dressing, if any, is removed from the wound site and the slurry is applied over the established or establishing layer of dermal fibroblasts to regenerate the outer skin layer thereby establishing a protective barrier of intact skin.

Once the epidermal cell slurry has been applied to the wound a gas-permeable wound dressing may be used to cover the skin injury. The epidermal cells then migrate and grow off the microspheres into the surrounding tissue to produce a continuous surface in replacement of the skin injury. As the cells grow, in vivo resorption of the microspheres commences.

A certain percentage of the epidermal cells may be treated either in vivo or in vitro with specific agents such as calcium and/or cAMP to accelerate production of a stratum corneum, the uppermost layer of dead, highly keratinized cells. The stratum corneum helps to regulate the amount of water lost from the body and also to prevent microbial invasion into the wound site. By controlled acceleration of the differentiation of this layer, the repaired wound site will function more like uninjured, intact skin.

In another embodiment of the present invention, cells from both the dermal and the epidermal layers are co-cultured in a tissue culture flask. This embodiment can provide for enhanced paracrine and autocrine function development. Using the same tecnniques as discussed earlier, the cells are then removed from the tissue culture flask and seeded in a bioreactor containing cell culture medium and microspheres. The cells are allowed to attach to the microspheres under static or semi-static conditions for subsequent co-culture in suspension in a bioreactor. An individual microsphere may then have cells from both the dermal and epidermal layers attached thereto. The resulting microsphere/cell slurry is applied directly on the wound in much the same way as a salve or paste would be applied for regeneration of the dermal and epidermal layers simultaneously. As occurs in vivo, the differentiating keratinocytes tend to migrate to the uppermost regions of the wound site leading to a natural formation of a stratum corneum. A gas-permeable wound dressing may then be used to cover the skin injury site until the wound is effectively healed by the normal reformation of the dermal and epidermal components.

In a further embodiment of the present invention, dermal fibroblasts and cells derived from the epidermal layer are cultured independently in separate tissue culture flasks. The dermal fibroblasts are removed from its tissue culture flask using, for example, trypsin and seeded in a vessel containing an appropriate cell culture medium and microspheres. The dermal fibroblasts are then allowed to attach to the microspheres under static or semi-static conditions.

Likewise, the epidermal cells, including keratinocytes, are removed from its tissue culture flask using, for example, trypsin and seeded in another vessel containing an appropriate cell culture medium and microspheres. The epidermal cells are then allowed to attach to the microspheres under static or semi-static conditions.

The microspheres coated with dermal fibroblasts and the microspheres coated with epidermal cells are then introduced into a single bioreactor for subsequent co-culture thereof. The resulting slurry of cell-coated microspheres is then applied to the wound for simultaneous regeneration of the dermal and epidermal layers. A gas-permeable wound dressing may then be applied to cover the wound.

In a still further embodiment, dermal fibroblasts are attached to microspheres and allowed to proliferate in a bioreactor. After a period of time, cells from the epidermal layer are seeded into the bioreactor for subsequent attachment to the microspheres already coated to some degree with dermal fibroblasts. The keratinocytes can thereby benefit from the paracrine effects of the fibroblasts.

The present invention can also be used for implants in vivo of melanocytes for imparting natural pigmentation to the skin and providing UV protection.

In cosmetic applications, for example the repair of severe scarring due to wounds, acne, etc., the epidermal layer and optionally a small percentage of the underlying dermal layer can be surgically removed using a dermatome or other suitable surgical instrument. Subsequently, a slurry of cell-coated microspheres is applied directly to the pretreated area in one or more layers to correct contour variations.

The microspheres used in the present invention can be made of a variety of materials which are biocompatible and capable of being readily resorbed into the body by natural in vivo enzyme action without the formation of toxic by-products. suitable materials for the microspheres include natural and synthetically-derived bioresorbable materials such as polyhydroxybutyrate (PHB), PHB-polyhydroxyvalerate (PHB-PHV) copolymers, PHB having polyester bonds, lactide-glycolide polymers, lipids, phospholipids, polylactones, polyesters, polylactides, polyglycolides, polyanhydrides, collagen, gelatin and other resorbable materials not having an adverse effect on tissues during healing (i.e. not toxic to the cells as presented initially or through the end products of resorption). These materials can be used in pure form or as a blend of materials to enhance physiochemical properties or to control degradation rates thereof.

Preferably, the microspheres have a density of between 1.01 to 1.04 g/ml in order to facilitate mixing and suspension in culture media. The microspheres can be relatively smooth, or have some surface variability, with a macroporosity of between 30 and 80% and a range of porosity of 30 to 80 $\mu$m. The microspheres have a relatively high surface area, for example, about 5000 $cm^2$/g dry weight, compared with the mesh matrices of the prior art planar technologies, which generally have surface areas in the range of 200–700 $cm^2$/g. Moreover, a greater amount of material is required to impart adequate strength to the mesh matrix. Accordingly, significantly more material would be required to provide an implant for the same surface area and, likewise, more material would have to be resorbed in vivo with the mesh matrix.

It will be appreciated by those skilled in the art that other structures such as wafers, cylinders and ovoids can also be used in the living skin replacement of the present invention in place of microspheres.

The microspheres can also be formed with a core of one material and an outer layer or coating of another material to improve the microsphere resorbability and functionality, including charge density, attachment of other chemicals or compounds, and enhancement of cell attachment and spreading. For example, a coating of phospholipid allows for the generation of a polar surface with the functional phosphate head group. Also, the acyl group of the phospholipid provides a more hydrophobic surface for the microsphere. Various chemicals or biomolecules can then be attached to these portions of the phospholipids. In addition, certain stratum corneum lipids including phospholipids and sphingosines can be coated onto microspheres to impart antimicrobial activity. Sphingosines are particularly good at inhibiting microbial growth at µg levels ("Antimicrobial activity of sphingosines" *J Invest Dermatol* 98:269–273; 1992).

Figure 6:
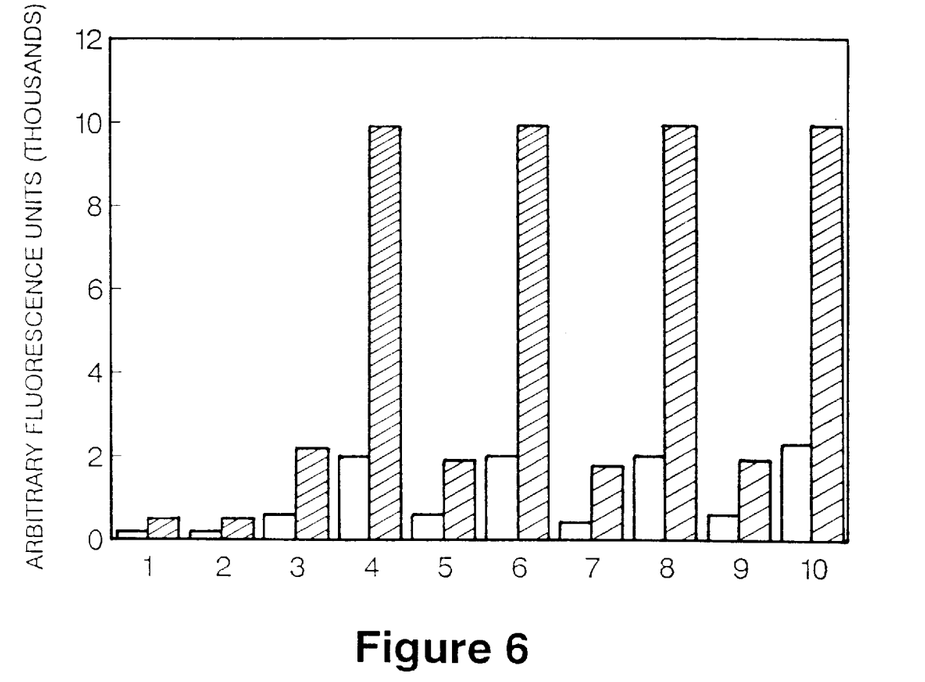
FIG. 6 is a histogram of data obtained from a cytofluorometer.

FIG. 6 is a histogram of data produced by a cytofluorometer for measuring cell viability. Cell viability is measured with a fluorochrome specific to viable cells and a fluorochrome specific to dead cells. These measurements are expressed as "Arbitrary Fluorescence Units" and are plotted on the histogram with cross-hatched bars representing viable cells and blank bars representing dead cells. Interpretation of the data is corrected by data sets 1 and 2 for phosphate buffer solution and the control, respectively.

Keratinocytes from the same cell inoculum were seeded on PHB and on PHB coated with a phospholipid and, in each case, incubated for 24 hours. Cell viability of the attached cells was measured by introducing the above-mentioned fluorochromes to the appropriate sample. Samples without cells attached thereto were also treated with the fluorochromes to provide further correction for the specific resorbable material. The cell-free samples are presented in data sets 3, 5, 7 and 9 which provide correction factors for data sets 4, 6, 8 and 10, respectively.

Data sets 4 and 8 represent the viability of keratinocytes attached to PHB, while data sets 6 and 10 indicate PHB coated with a phospholipid. The resorbable materials of data sets 3, 4, 5 and 6 were autoclaved prior to seeding with cells while the resorbable materials of data sets 7, 8, 9 and 10 were sterilized by a non-thermal ethylene oxide process. The data indicates that the cells are highly viable on these resorbable materials. Furthermore, the method of presterilization (by steam or ethylene oxide) does not affect the attachment efficiency or viability of the cell populations.

In another embodiment, the microsphere is formed by combining the polysaccharide and the resorbable material so that the resorbable material is randomly distributed through the core. The polysaccharide (such as, dextran or starch) can be eroded or chemically or enzymatically digested away before the stage of coating of the microsphere with skin cells, leaving an open structure for enhanced hydrolysis of the resorbable material once in vivo. This type of microsphere reduces diffusional limitations of nutrients or metabolic byproducts, thereby further facilitating growth of cells. Additionally, various growth or other factors incorporated in or on the microsphere are released more rapidly, thereby allowing for "access" to these factors at the appropriate time during the healing process.

Alternatively, the microsphere can be used with the polysaccharide component intact for resorption during cell proliferation in vitro and in vivo.

In a preferred embodiment of the present invention the microspheres resorb at a rate comparable to cell population expansion. In this way, as the microspheres are resorbed, the cells grow into the small voids left by the partially resorbed microsphere thereby minimizing scarring and contour variations.

One approach to the choice of materials and/or factors or coatings is to choose one combination for the dermal layer and another for the epidermal layer. Preferably, the microspheres in the epidermal layer resorb much more rapidly than the underlying material for the dermal layer. This allows the keratinocytes to migrate and spread on the underlying dermal layer in a more natural manner. It is possible that the coatings are different for the different types of cells although one type of coating may be suitable.

Microspheres can have other features imparted to them by incorporating additives in or on the microspheres, for example by immobilization, encapsulation, covalent linking, or by simple adsorption. These additives are used to enhance cell proliferation, to improve the local environment in vivo following implantation, and/or to control release of certain agents. Such additives can be incorporated in or on substantially all microspheres of an implant or onto only a proportion thereof.

For example, the controlled release of antimicrobial agents is particularly important as the majority of these compounds are cytotoxic to both dermal fibroblasts and keratinocytes at the therapeutic levels currently used clinically, resulting in a profound negative effect on wound healing. Better controlled release of antimicrobial agent can be achieved by prior treatment of the microspheres with the antimicrobial agent, resulting in less detriment to the healing of the wound while asepsis is maintained.

Figure 7:
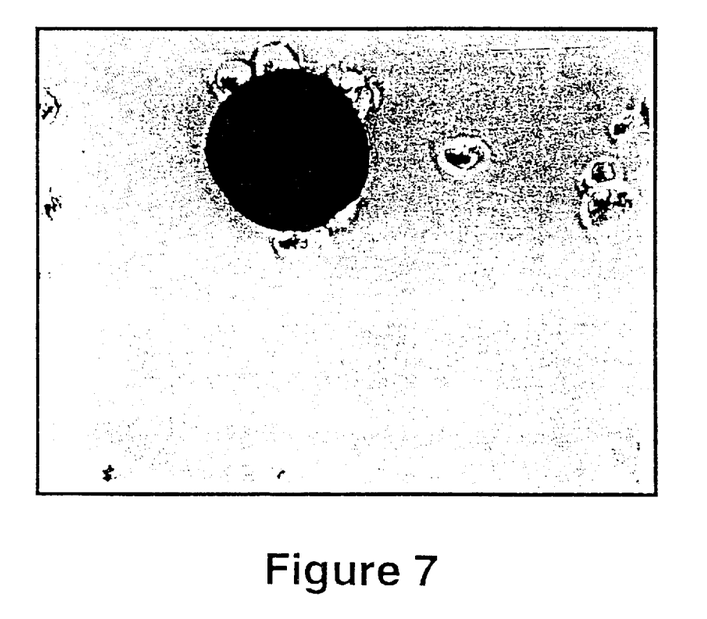
FIG. 7 is a micrograph showing dermal fibroblasts attached to microspheres treated an attachment factor at 1 hour post cell-seeding.
Figure 8:
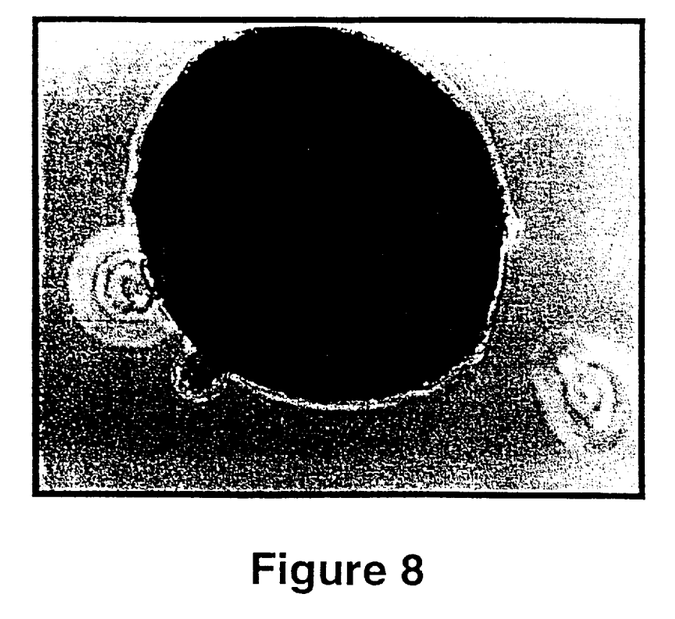
FIG. 8 is a micrograph showing the dermal fibroblasts attached to microspheres treated with the attachment factor of FIG. 7 at 22 hours post cell-seeding.

Alternatively, the surface of the microspheres can be pre-treated to enhance attachment of cells thereto, for example, with an attachment factor such as arginineglycineaspartic acid tripeptide (RGD), or poly-L-lysine. FIG. 7 is a micrograph showing neo-natal foreskin derived dermal fibroblasts attached to PHB-PHV microspheres treated with RGD attachment factor at 1 hour post cell-seeding. FIG. 8 is a micrograph showing the dermal fibroblasts attached to PHBPHV microspheres treated with RGD of FIG. 7 at 22 hours post cell-seeding. The majority of the cells that have attached to the microsphere are flattened and no longer spherical.

Figure 9:
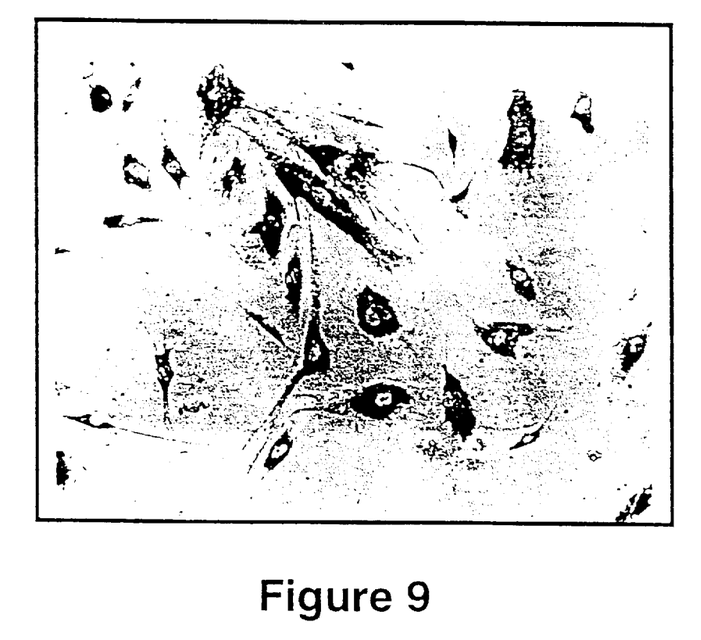
FIG. 9 is a micrograph of dermal fibroblasts attached to a glass surface (control)
Figure 10:
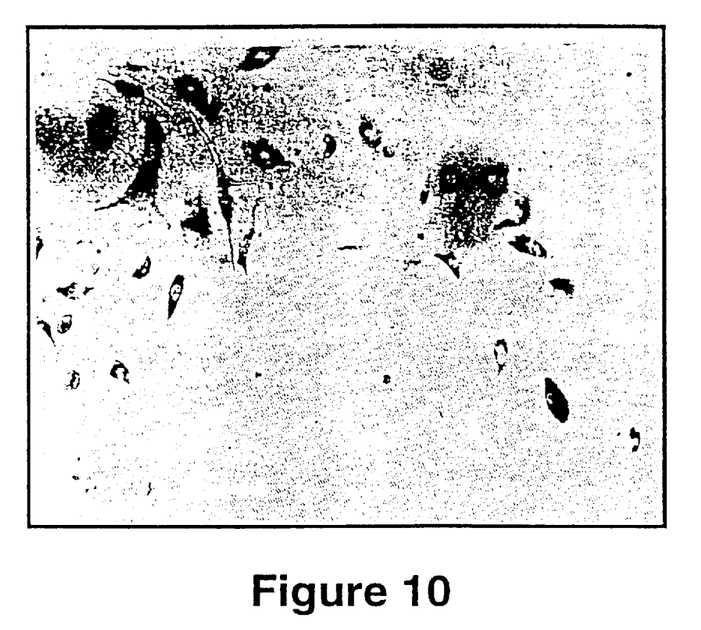
FIG. 10 is a micrograph of dermal fibroblasts attached to a planar surface of PHB-PHV (polyhydroxybutyratepolyhydroxyvalerate copolymer)
Figure 11:
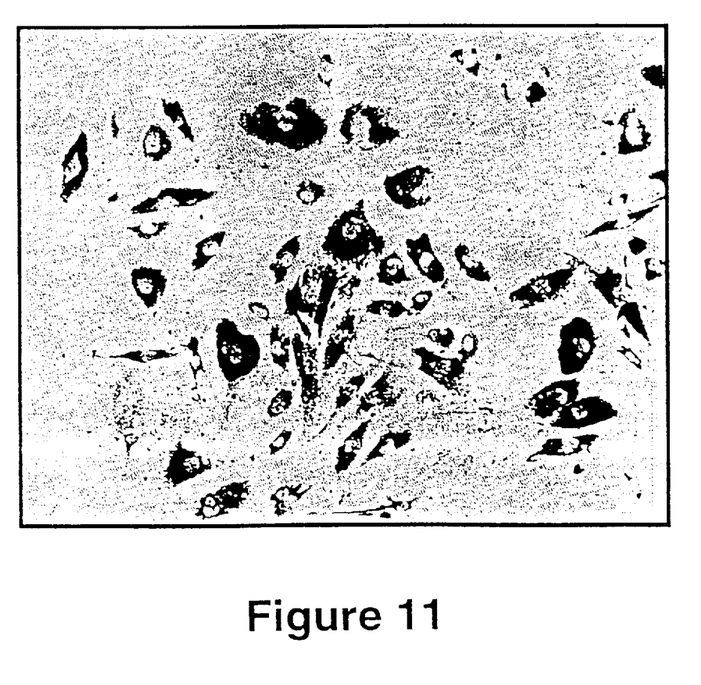
FIG. 11 is a micrograph of dermal fibroblasts attached to a planar surface of PHB-PHV treated with an attachment factor.

FIG. 9 is a micrograph of neo-natal foreskin derived dermal fibroblasts attached to a glass surface (control) and incubated for 26 hours. FIG. 10 is a micrograph of neo-natal foreskin derived dermal fibroblasts attached to a planar surface of PHB-PHV and incubated for 26 hours. FIG. 11 is a micrograph of neonatal foreskin derived dermal fibroblasts attached to a planar surface of PHB-PHV treated with RGD and incubated for 26 hours. The viable cells in FIGS. 9, 10 and 11 are stained with Neutral Red. The dye is actively taken up by viable cells to demonstrate, in FIGS. 10 and 11, that the cells are highly viable on the bioresorbable materials used.

Other factors which can be incorporated into the microspheres include growth factors, such as epidermal growth factor (EGF), transforming growth factor-alpha (TGF-A), tansforming growth factor-beta (TGF-beta), keratinocyte growth factor (KGF), basic fibroblast growth factor (bFGF), and insulin-like growth factor-I (IGF-I). A controlled delivery of these factors can be obtained by the use of microspheres in order to obtain better control of wound healing, since if delivery of mitogenic (growth) or angiogenic (inducing recapillarization of the wound) factors is too rapid, scarring of the wound site can occur. Growth factors can also be immobilized onto the surface of the microspheres with, for example, a permanent covalent linkage so that the cells contact the immobilized growth factor.

Monoclonal antibodies can be incorporated onto the microspheres to control the local in vivo levels of TGF-beta, for example, in order to avoid an over-abundant supply of this 15 factor at a particular point in the wound healing process. TGF-beta, if available in excess amounts, can lead to a disproportionate excess of collagen production by fibroblasts and macrophage cells.

Resorption of the microspheres can be enhanced by incorporating enzymes such as lipase, depolymerase, and dehydrogenase into the microspheres. These enzymes enhance the resorption by other endogenous enzymes in vivo or free radicals generated by the body (e.g. macrophage cells) which can attack the structural linkages leading to depolymerization of the bioresorbable material.

It is also possible that some substances linked to the microspheres, or incorporated in them, may be derived directly from the patient. For example, platelet derived growth factor (PDGF) (which is known to promote wound healing) can be derived from the patient's blood platelets and complexed within or onto the microspheres. The blood sample required is relatively small, for example, 100–200 ml.

Other additives include polyamines to mitigate hypertrophic scarring, materials which impart biostatic, microbicidal or anti-rejection properties, and proteinoids, for enhanced activity and/or stability.

Additionally, growth, migration, angiogenesis and other factors can be incorporated in or on a further supply of microspheres that are not intended to be cell-coated. For this purpose it is possible to use ultra small microspheres as these are not required in large quantities thereby reducing the amount of material for resorption. These ultra small microspheres with diameters ranging from 10 to 50 microns can be interspersed with the larger cell-coated microspheres into the wound site or added independently at a suitable time. The surrounding tissues may be pretreated with chemotactic, angiogenic, and mitogenic factors coated on the surface of such cell-free microspheres in order to improve the environment for cell migration, nutrient delivery, migration and growth. It is another advantage of the present invention that, although many of these factors have a relatively short stability in solution, they can be prepared fresh just before treatment of the wound with the cell-coated microspheres. These particular microspheres can be interspersed and delivered at the time the cells are delivered or alternatively earlier, in order to establish an environment encouraging cellular migration, angiogenesis and/or proliferation. A programmed environment can thereby be established for accelerated tissue regeneration and migration in the wound site. As a result, the underlying capillary network could be augmented for "normal" delivery of nutrients to applied cells.

Important advances have been made in the last few years in the formulation of culture media that do not contain animal-derived sera. This is particularly important for technologies destined for human clinical applications. Serum, typically derived from bovine sources, is not only quite undefined but it can also lead to entry of contaminants into the final product and account for variable results. Defined serum-free media are suitable for the cultivation of dermal fibroblasts and keratinocytes. Numerous serum-free media are commercially available including, for example, Clonetics Corporation KGM, FGM and GIBCO KGM.

In the co-culture of keratinocytes and dermal fibroblasts, keratinocytes require lower levels of calcium in the medium to encourage rapid growth rates and prevent terminal differentiation. Under higher levels of calcium (>0.1 mM), the keratinocytes tend to grow slowly and to undergo terminal differentiation leading to apoptosis (programmed cell death).

Dermal fibroblasts are usually grown in media with calcium levels in the range of 1 to 3 mM to allow for normal growth and function. Accordingly, in one embodiment the dermal fibroblasts are first cultured in a medium containing calcium in a concentration greater than 0.1 mM. After a period of time, the cells are washed with a phosphate buffered saline (PBS) solution in situ to remove the growth medium. Keratinocytes and a different medium with a reduced calcium concentration are then added to the tissue culture flask containing the cultured dermal fibroblasts. The net result in further culturing is a slowing down of the fibroblast growth while allowing for good keratinocyte growth. This is an ideal situation as it allows for a layer of keratinocytes to grow in the presence of the fibroblasts without the fibroblasts overgrowing the keratinocytes. The fibroblasts, while not proliferating, can still produce factors required by the keratinocytes for optimal growth and organization on the dermal surface. Factors produced by fibroblasts that can enable optimal keratinocyte growth/organization include fibronectin and TGF-beta.

The present invention provides potential for geographical centralization of wound or burn treatment facilities for the actual cell manipulation. Application of the dermal fibroblasts to full- and partial-thickness skin injuries can be expedited with the maintenance of a local "bank" of donor-derived, including cadaver-derived, dermal fibroblasts which exhibit very low allergenicity in transplants.

A tissue explant derived from the patient can then be shipped in an appropriate transport medium similar to that used for transporting organs for transplant (such as, ViaSpan (trade-mark) UW Solution (Dupont), or other maintenance medium) to a central cell processing facility for culture of the keratinocytes while the patient is already being treated with a dermal fibroblast/microsphere slurry. Typically, a 4 $cm^2$ tissue explant could be rapidly transported and expanded to treat an equivalent tissue area of several square meters within 1 to 3 weeks if required. The growth of sufficient cells for treatment is markedly faster and more effective than the conventional approaches outlined.

Once a suitable size cell population is obtained, the cell-coated microspheres can be harvested, concentrated and put into a maintenance medium for shipment to the remote treatment center. Large numbers of cells, in the order of $10^7$ cells/ml, can be transported on the microspheres in a relatively small volume. This is an advantage over the planar technology which requires a larger number of containers for the equivalent amount of cells. Furthermore, the transport of the mesh matrices is hampered by the fragile nature of the tissue preparation. The microsphere/cell slurry of the present invention is less fragile and can still be satisfactorily shipped under less than ideal conditions.

Cell-coated microspheres can be transported in medium similar to that used for transport of transplant organs such as heart. Moreover, the medium can be adapted to include perfluorocarbons for enhanced oxygen transfer. The microsphere/cell slurry requires little or no further treatment before application to the skin injury. Known technologies such as tangential- or cross-flow membranes or hollow fibre membranes can also be used in transport thereby retaining the cells/microspheres while manipulating the environment in which they reside.

The mesh matrix implants discussed previously are typically cryo-preserved to enable transport thereof. However, it will be appreciated by those skilled in the art that cryo-preserving medium may include dimethylsulfoxide (DMSO) which 30 requires elaborate techniques including a sterile environment and numerous manipulations, requiring a tissue culture laboratory at the receiving end for the removal thereof before implant. This type of facility may not always be available on site when or where treatment is required.

INDUSTRIAL APPLICABILITY

The present invention allows for fast and effective treatment of full- and partial-thickness skin injuries, such as burns and other wounds. Unlike conventional methods, the present invention does not require the use of stapling, suturing, or other attachment methods for application to the patient, nor is it constrained by problems associated with body profiling or curvature. Furthermore, the application of the microsphere/cell slurry can be conducted under both ideal and less than ideal conditions.

The living skin replacement of the present invention can also be used as a "skin model" in risk and safety assessment assays for pharmaceutical, cosmetic and household compounds. This is a growing area owing to the demand to circumvent animal testing.

The present invention also finds utility in the cosmetic sector for correcting skin defects.

I claim:

1. A living skin replacement composition for full-thickness and partial-thickness skin injuries which adapts to the shape of said injuries, said composition comprising a slurry of a biologically acceptable liquid carrier, microspheres, said microspheres comprising a material which is biocompatible and resorbable in vivo, said microspheres having a macroporosity of 30 to 80%, and proliferative skin cells selected from the group consisting of keratinocytes, dermal fibroblasts, melanocytes and combinations thereof coating said microspheres wherein when said slurry is applied to an injury, said proliferative skin cells migrate from said microspheres to said injury.

2. A living skin replacement composition according to claim 2, wherein said skin cells are dermal fibroblasts.

3. A living skin replacement composition according to claim 1, wherein said skin cells are kratinocytes or melanocytes.

4. A living skin replacement composition according to claim 1, wherein skin cells are a combination of dermal fibroblasts, keratinocytes and melanocytes.

5. A living skin replacement composition according to claim 1, wherein the cells are obtained from a patient with a skin injury.

6. A living skin composition according to claim 1, wherein the skin cells are obtained from a donor other than a patient with skin injury.

7. A living skin replacement composition according to claim 1, wherein the microspheres are formed of at least one material selected from the group consisting of polyhydroxybutyrate (PHB), PHB-polyhydroxyvalerate (PHB-PHV) copolymers, lactide-gylcolide polymers, lipids, polylactones, polyesters, polyactides, polyglycolides, polyanhydrdes, collagan, and gelatin.

8. A living skin replacement composition according to claim 7, wherein the microspheres are formed of a core of one material and a coating of another material.

9. A living skin replacement composition according to claim 8, wherein the microspheres are coated with a phospholipid or a sphingosine.

10. A living skin replacement composition according to claim 1, wherein the micropheres are formed of polyhydroxybutyrate and polysaccharide.

11. A living skin replacement composition according to claim 10, wherein the polysaccharide is eroded or chemically or enzymatically removed prior to coating the microspheres with cells.

12. A living skin replacement composition according to claim 25, wherein the polypeptide is incorporated in or on the micropheres prior to coating the microspheres with skin cells.

13. A living skin replacement composition according to claim 1, further comprising a second microsphere comprising an additive in or on said second microsphere.

14. A living skin composition according to claim 1, wherein the average diameter of the microspheres is in the range of about 10 to 500 $\mu$m.

15. A living skin replacement composition according to claim 13, wherein the average diameter of the additional microspheres is in the range of about 10 to 500 $\mu$m, preferably about 10 to 50 $\mu$m.

16. A process for the production of a living skin replacement composition comprising the steps of culturing skin cells selected from the group consisting of keratinocytes, dermal fibroblasts, melanocytes and combinations thereof, providing a plurality of biocompatible, resorbable microspheres having a macroporosity of 30 to 80%, attaching said skin cells to said microspheres, and growing said attached skill cells to confluence or near confluence in a growth medium to yield microspheres coated with proliferative skin cells, and thereafter concentrating said cell-coated microspheres into a slurry in a biologically acceptable liquid carrie, wherein when said cell-coated microspheres are applied to a skin injury, said proliferative cells migrate from said microspheres to said injury.

17. A process according to claim 16, wherein a combination of dermal fibroblasts and keratinocytes is employed and said step of growing cells comprises growing dermal fibroblasts in a first medium containing calcium in a concentration greater than about 0.1 mM, and subsequently washing said cells with a buffer solution to remove said first medium, and growing keratinocytes in a second medium containing calcium in a concentration less than about 0.1 mM.

18. A process according to claim 16, wherein the growth medium is serum-free.

19. A method of treating a full-thickness or partial-thickness skin injury with a living skin replacement composition which adapts to the shape of said injury, comprising the steps of growing skin cells selected from the group consisting of dermal fibroblasts, keratinocyte melanocytes and combinations thereof on biocompatible, resorbable microspheres having a macroporosity of 30 to 80% in a medium, concentrating said microspheres coated with proliferative skin cells into a slurry in a biologically acceptable liquid carrier, and applying said slurry of cell-coated microspheres onto an area of skin injury, wherein said proliferative skin cells migrate from said microspheres to said injury.

20. A method according to claim 19, further comprising the steps of growing keratinoytes, melanocytes or a combination thereof on biocompatible, resorbable microspheres having a macroporosity of 30 to 80% in a medium, concentrating said microspheres coated with keratinocytes, melanocytes or a combination thereof into a second slurry in a biologically acceptable liquid carrier, and overlaying said second slurry onto said area of skin injury to which microspheres coated with skin cells have already been applied.

21. A method according to claim 19, wherein a combination of dermal fibroblasts, keratinocytes and melnanocytes is employed and said dermal fibroblasts are attached to said microspheres and after a period of time said keratinocytes, melanocytesor a combination thereof are attached to said microspheres coated with said dermal fibroblasts.

22. A method according to claim 19, further comprising the steps of correcting contour variations with subsequent applications of cell-coated microspheres onto the area of skin injury.

23. A method according to claim 19, further comprising the step of correcting contour variations with subsequent applications of cell-coated microspheres onto the area of skin injury.

24. A living skin replacement composition according to claim 1, wherein one or more additives are incorporated in or on the microsphere.

25. A living skin replacement composition according to claim 24, wherein an additive comprises a polypeptide.

26. A living skin replacement composition according to claim 24, wherein an additive comprises an antimicrobial agent.

27. A living skin replacement composition according to claim 24, wherein an additive comprises a polyamine.

28. A living skin replacement composition according to claim 24, wherein an additive comprises a drug.

29. A living skin replacement composition according to claim 28, wherein said drug is an immunosuppressant.

30. A living skin replacement composition according to claim 24, wherein an additive comprises a carbohydrate.

31. A living skin replacement composition according to claim 24, wherein an additive comprises a lipid.

32. A living skin replacement composition according to claim 24, wherein an additive comprises a pigment.

33. A living skin replacement composition according to claim 25, wherein said polypeptide is collagen.

34. A living skin replacement composition according to claim 25, wherein the polypeptide is selected from the group consisting of lipase, depolymerase, and dehydrogenase.

35. A living skin replacement composition according to claim 25, wherein the polypeptide is a platelet derived growth factor.

36. A living skin replacement composition according to claim 35, wherein the platelet derived growth factor is patient-derived.

37. A living skin replacement composition according to claim 25, wherein the polypeptide is selected from the group consisting of epidermal growth factor, transforming growth factor-alpha, transforming growth factor-beta, insulin-like growth factor, keratinocyte growth factor and basic fibroblast growth factor.

38. A living skin replacement composition according to claim 25, wherein the polypeptide arginine-glycine-aspartic acid tripetide or poly-L-lysine.

* * * * *